United States Patent [19]

Curran

[11] B 4,001,330
[45] Jan. 4, 1977

[54] AMINO ETHANOL-INDANE AND TETRAHYDRONAPHTHALENE DERIVATIVES

[75] Inventor: Adrian Charles Ward Curran, Reading, England

[73] Assignee: John Wyeth & Brother, Ltd., Maidenhead, England

[22] Filed: May 23, 1974

[21] Appl. No.: 472,760

[44] Published under the second Trial Voluntary Protest Program on April 13, 1976 as document No. B 472,760.

[30] Foreign Application Priority Data

June 7, 1973 United Kingdom ............ 27123/73

[52] U.S. Cl. .................... 260/570.6; 260/348 R; 260/348.6; 260/501.18; 260/501.19; 260/567.6 M; 260/570.5 C; 260/592; 260/618 F; 424/316; 424/330

[51] Int. Cl.² ........................................ C07C 91/22

[58] Field of Search ...... 260/501.18, 570.6, 501.19

[56] References Cited

UNITED STATES PATENTS 3,255,249  6/1966  Howe et al. ............... 260/570.6 X Primary Examiner—Robert V. Hines

[57] ABSTRACT

The invention provides novel indane and tetrahydronaphthalene derivatives having the general formula

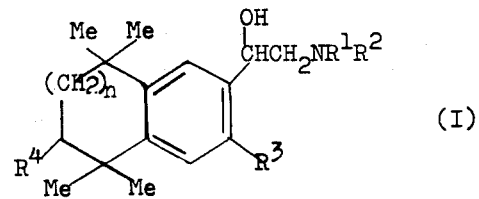

wherein $R^1$ represents hydrogen or lower alkyl; $R^2$ represents lower alkyl; $R^3$ and $R^4$ independently represent hydrogen or lower alkyl; and $n$ is the integer 1 or zero; and the pharmaceutically acceptable acid addition and quaternary ammonium salts thereof; which have hypotensive activity.

4 Claims, No Drawings

AMINO ETHANOL-INDANE AND TETRAHYDRONAPHTHALENE DERIVATIVES

This invention relates to indane and tetrahydronaphthalene derivatives, and to pharmaceutical compositions containing them.

In particular this invention provides novel indane and tetrahydronaphthalene derivatives having the general formula:

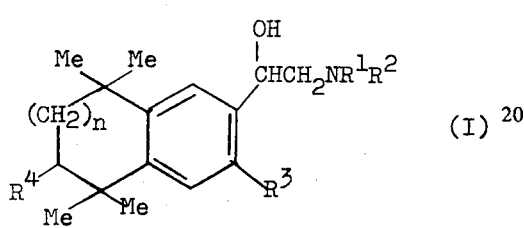

(I)

wherein $R^1$ represents hydrogen or lower alkyl; $R^2$ represents lower alkyl; $R^3$ and $R^4$ independently represent hydrogen or lower alkyl; and n is the integer 1 or zero; and the pharmaceutically acceptable acid addition and quaternary ammonium salts thereof.

The term "lower alkyl" used herein signifies that the radical contains up to 6 carbon atoms.

Examples of the group $R^1$ are hydrogen, methyl, ehtyl, n-propyl, iso-propyl, n-butyl, sec-butyl and tert-butyl. Preferably $R^1$ is hydrogen. Examples of $R^2$ are methyl, ethyl, n-propyl, isopropyl, n-butyl, sec-butyl and tert-butyl. Examples of $R^3$ are hydrogen, methyl, ethyl, n-propyl and n-butyl. Preferably $R^3$ is hydrogen or methyl. Examples and preferred groups for $R^4$ are the same as for $R^3$. The acid addition salts of this invention include salts formed with inorganic acids such as hydrochlorides, hydrobromides or sulphates, nitrates, phosphates, or salts formed with organic acids such as acetates, citrates, tartrates, maleates, fumarates, formates, sulphonates, e.g. methane sulphonate and p-toluene sulphonate.

The novel compounds provided by the present invention possess hypotensive and cardioinhibitory activity when administered to warm-blooded animals and some are also intermediates for other compounds of the invention.

For example 1-[7-(1,1,3,4,4,6-hexamethyl)-1,2,3,4 tertrahydronaphthyl]-2-isopropylamino ethanol showed significant hypotensive activity when administered intravenously to normotensive anaethetised rats at a dose level of 3.2 mpk, and also cardioinhibitory activity when tested on guinea pig spontaneously beating atria. Further this compound did not exhibit β-adrenergic blocking activity when tested either on guinea pig spontaneously beating atria or on guinea pig isolated trachea and therefore the observed hypotensive and cardioinhibitory activities appear to act by some mechanism other than β-blockade.

A first general method of preparation of the compounds of general formula I comprises reducing a compound of general formula:

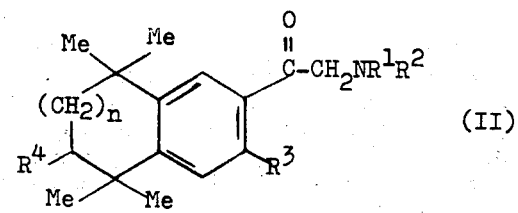

(II)

wherein $R^1$, $R^2$, $R^3$, $R^4$ and n are as defined above. Any reducing agent known in the art for reducing a ketone to a secondary alcohol may be used in the above reaction. For example the reduction process may be carried out using sodium borohydride or aluminium isopropoxide, in the presence of an inert solvent, for example methanol or using lithium aluminium hydride in the presence of an inert solvent, for example ether or tetrahydrofuran. Other hydride transfer agents may be used. Alternatively catalytic hydrogenation may be used to effect reduction, for example using palladium charcoal as catalyst in the presence of an inert solvent, for example aqueous methanol.

A second general method for the preparation of the compounds of formula I comprises reacting a compound of general formula:

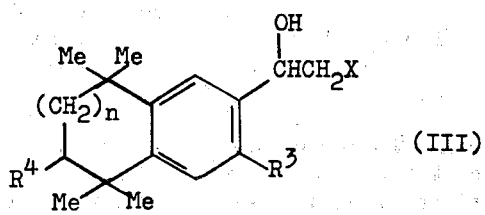

(III)

wherein $R^3$, $R^4$ and n have the same meanings as above and X is a halogen atom, with an amine of general formula:

$$HNR^1R^2 \quad\quad (IV)$$

wherein $R^1$ and $R^2$ have the same meanings as above. The process above may be carried out in the presence of an inert solvent, for example a lower alkyl alcohol, e.g. methanol or ethanol, and with heating if desired. In this process preferred halogens as defined by X are chlorine and bromine. It is understood that in the process above the compound of formula III may eliminate HX during the reaction with the amine of formula (IV) to produce a compound of general formula:

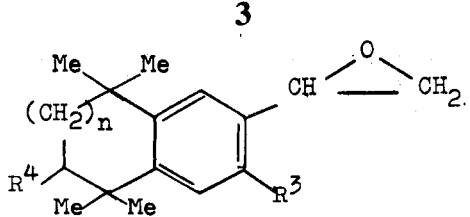

(V)

wherein $R^3$, $R^4$ and n are as defined above, which then reacts with the amine of general formula (IV) to produce compounds of general formula (I).

The starting materials of general formulae (II) and (III), used in the two processes for the preparation of the novel compounds of this invention described above, may each be prepared from a haloacetyl compound of general formula:

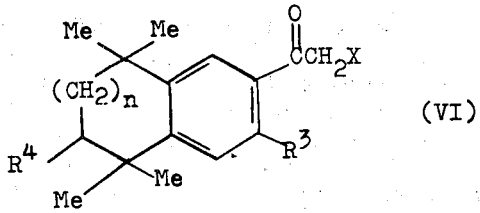

(VI)

wherein $R^3$, $R^4$, n and X are as defined above, by
i. reaction with an amine of general formula:
$$HNR^1R^2 \quad (IV)$$
wherein $R^1$ and $R^2$ are as defined above, to give a compound of general formula (II); or by
ii. reduction to give a compound of general formula III. For both processes described above preferred halogens, as defined by X, are chlorine and bromine.

In connection with process (i) an inert solvent may be used, for example, ethanol. In connection with process (ii) the reduction may be effected by the use of reducing agents such as sodium borohydride or aluminium isopropoxide in the presence of an inert solvent such as a lower alkyl alcohol, e.g. methanol, ethanol or isopropanol, or cyclohexane.

The compounds of general formula (VI) are also novel compounds within the scope of this invention.

They may be prepared from starting material of general formula:

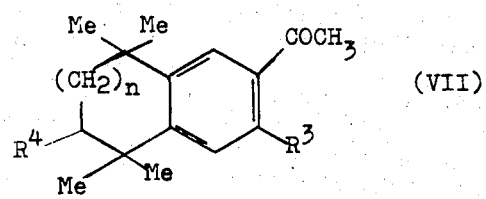

(VII)

wherein $R^3$, $R^4$ and n are as defined above, by monohalogenating the α-carbon atom of the ketone using methods known in the art. For example a preferred process for the above reaction is to halogenate, for example with bromine, the compound of general formula (VII), in the presence of glacial acetic acid. Alternatively bromination may be accomplished by refluxing with N-bromosuccinimide in an inert solvent, for example carbon tetrachloride.

A further process for the preparation of compounds of general formula I in which $R^1$ represents hydrogen and $R^2$ represents normal or secondary lower alkyl comprises reacting under reducing conditions a compound of general formula:

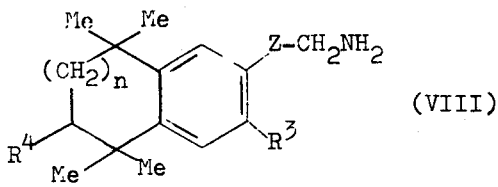

(VIII)

wherein $R^3$, $R^4$ and n are as hereinbefore defined and Z represents a -CO-or-CHOH-group with an aldehyde or ketone of general formula:

(IX)

wherein $R^5$ is hydrogen, or a methyl or ethyl group and $R^6$ is hydrogen, or an alkyl group of 1 to 3 carbon atoms which may be branched or straight chain.

Examples of suitable reducing conditions are those provided by the presence of a hydrogenation catalyst, for example platinum oxide, hydrogen, and an excess of the carbonyl compound. Other catalysts include nickel or palladium, e.g. palladium charcoal. Alternatively a hydride transfer agent such as sodium borohydride may be used.

When a compound of general formula I is prepared which is in the form of the primary amine then that compound may be converted to other compounds of formula I which are secondary or tertiary amines by reaction with an organo-halide of general formula $R^1X$ wherein $R^1$ is lower alkyl and X is a halogen. In similar manner a secondary amine of general formula I may be converted to a tertiary amine of general formula I by reaction with an organohalide of general formula $R^1X$, wherein $R^1$ and X are as defined above.

A further aspect of the invention is the provision of a pharmaceutical composition comprising a compound of general formula I, or a pharmaceutically acceptable acid addition or quaternary ammonium salt thereof, together with a pharmaceutical carrier. Any suitable carrier known in the art may be used to prepare the pharmaceutical compositions. In such a composition the carrier may be solid, liquid or a mixture of solid and liquid. In the solid form the compositions include powders, tablets and capsules. In the liquid or solid/liquid form the compositions include solutions, suspensions and creams.

When the compounds of this invention are employed as hypotensive agents they may be administered to warm-blooded animals, e.g. mice, rats, rabbits, dogs, cats or monkeys alone or in combination with pharmaceutically acceptable carriers, the proportion of which is determined by the solubility and chemical nature of the compounds, chosen route of administration and standard biological practice. For example, they may be administered orally in the form containing such excipients for example as starch, milk or sugar, e.g. as tablets or capsules. They may also be administered orally in the form of solutions or they may be injected as solutions. For intraperitoneal administration they may be used in the form of sterile solutions or suspensions containing other solutes for example enough saline or glucose to make the solution isotonic.

The dosage of the present compounds will vary with the mode of administration and the particular compound chosen. Furthermore, it will vary with the particular subject under treatment. Generally, treatment is initiated with doses substantially less than the optimum dose of the compound. Thereafter, the dosage may be increased by small amounts until the optimum effect under the circumstances is reached. In general, the compounds of this invention are most desirably administered at a concentration level that will generally afford effective results without causing any harmful or deleterious side effects.

The following non-limiting examples illustrate the invention:

EXAMPLE 1

1-[7-1,1,3,4,4,6-Hexamethyl)-1,2,3,4-tetrahydronaphthyl]-2-isopropylamino ethanol.

1,1,3,4,4,6-Hexamethyl-7-acetyl-1,2,3,4-tetrahydronaphthalene (33 gm,0.12 m) was dissolved in glacial acetic acid (40 ml.) and the solution treated portionwise with bromine (20.3 gm) with stirring. The mixture was allowed to stand overnight at room temperature and poured onto ice (100 gm.). The resulting mixture was extracted with ether ( 3 ×100 ml.) and the combined extracts washed with saturated sodium carbonate (2 × 50 ml.) and then brine. The washed extracts were then dried (MgSO$_4$) and the solvent removed in vacuo to give a crystalline solid. This was recrystallised from absolute ethanol to give 1,1,3,4,4,6-hexamethyl-7-bromoacetyl-1,2,3,4-tetrahydronaphthalene as colourless needles (16 gm, 38%) m.p. 68°C. [Found: C, 64.40; H, 7.65%. C$_{18}$H$_{25}$BrO requires: C,64.09; H,7.47%].

A solution of 1,1,3,4,4,6-hexamethyl-7-bromoacetyl-1,2,3,4-tetrahydronaphthalene (3 gm.,0.0089 m) in methanol (50 ml) was treated with isopropylamine (20 ml.) and cooled to 0°C. The solution was treated with sodium borohydride (1 gm.) over 1 hour and the reaction mixture allowed to stand at 0°C for 2 days. The volatiles were removed in vacuo and the residual oil shaken with ether (50 ml.) and 2N HCl (20 ml.). The solid was filtered, washed with cold water (20 ml.) and ether (2 × 50 ml.) and then dried to give the title compound as the hydrochloride a white powder (1.5 gm.,50%)m.p. 233.5°C. [Found: C,71.74; H,10.26; N, 3.79%. C$_{21}$H$_{36}$NOCl requires C,71.25; H, 10.75; N, 3.96%].

EXAMPLES 2 to 9

By procedures analogous to Example 1 the following compounds are prepared as the hydrochlorides:
1-[7-(1,1,3,4,4,6-Hexamethyl)-1,2,3,4-tetrahydronaphthyl]-2-t-butylamino ethanol.
1-[7-(1,1,3,4,4,6-Hexamethyl)-1,2,3,4-tetrahydronaphthyl]-2-dimethylamino ethanol.
1-[7-(1,1,4,4,-Tetramethyl)-1,2,3,4-tetrahydronaphthyl]-2-isopropylamino ethanol.
1-[7-(1,1,4,4-Tetramethyl)-1,2,3,4-tetrahydronaphthyl-2-t-butylamino ethanol.
1-[7-(1,1,4,4-Tetramethyl)-1,2,3,4-tetrahydronaphthyl]-2-dimethylamino ethanol.
1-[6-(1,1,2,3,3,5-Hexamethyl)indanyl]-2-isopropylamino ethanol.
1-[6-(1,1,2,3,3,5-Hexamethyl)indanyl]-2-dimethylamino ethanol.
1-[6-(1,1,2,3,3,5-Hexamethyl)indanyl]-2-t-butylamino ethanol.

We claim:
1. A compound having the formula:

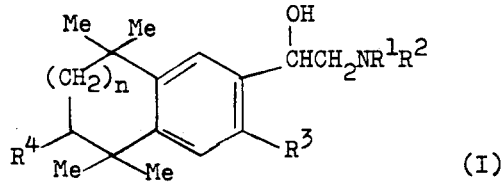

(I)

wherein R$^1$ represents hydrogen or lower alkyl; R$^2$ represents lower alkyl; R$^3$ and R$^4$ independently represent hydrogen or lower alkyl; and n is the integer 1 or zero; or a pharmaceutically acceptable acid addition salt thereof.

2. A compound as claimed in claim 1 wherein R$^1$ represents hydrogen or methyl; R$^2$ represents lower alkyl; R$^3$ and R$^4$ independently represent hydrogen or methyl; and n is the integer 1 or zero.

3. A compound as claimed in claim 1 wherein n is the integer 1.

4. A compound as claimed in claim 1 which is 1-[7-(1,1,3,4,4,6-hexamethyl)-1,2,3,4-tetrahydronaphthyl]-2-isopropylamino ethanol.

* * * * *